US009823098B2

(12) United States Patent
Bastianini

(10) Patent No.: US 9,823,098 B2
(45) Date of Patent: Nov. 21, 2017

(54) APPARATUS FOR INTERROGATING DISTRIBUTED OPTICAL FIBRE SENSORS USING A STIMULATED BRILLOUIN SCATTERING OPTICAL FREQUENCY-DOMAIN INTERFEROMETER

(71) Applicant: Filippo Bastianini, Bologna (IT)

(72) Inventor: Filippo Bastianini, Bologna (IT)

( * ) Notice: Subject to any disclaimer, the term of this patent is extended or adjusted under 35 U.S.C. 154(b) by 0 days.

(21) Appl. No.: 15/128,434

(22) PCT Filed: Apr. 23, 2015

(86) PCT No.: PCT/IT2015/000114
§ 371 (c)(1),
(2) Date: Sep. 23, 2016

(87) PCT Pub. No.: WO2015/170355
PCT Pub. Date: Nov. 12, 2015

(65) Prior Publication Data
US 2017/0108358 A1    Apr. 20, 2017

(30) Foreign Application Priority Data

May 5, 2014    (IT) .............................. BO2014A0262

(51) Int. Cl.
*G01D 5/353*      (2006.01)
*G01B 9/02*       (2006.01)
(Continued)

(52) U.S. Cl.
CPC ..... *G01D 5/35335* (2013.01); *G01B 9/02004* (2013.01); *G01B 9/0209* (2013.01);
(Continued)

(58) Field of Classification Search
CPC ........... G01D 5/35335; G01D 5/35303; G01D 5/35306; G01B 9/02004; G01B 9/0209;
(Continued)

(56) References Cited

U.S. PATENT DOCUMENTS

| 7,283,216 B1 | 10/2007 | Geng et al. |
| 2010/0002226 A1* | 1/2010 | Hartog ............... G01D 5/35364 356/73.1 |

(Continued)

FOREIGN PATENT DOCUMENTS

EP    2 110 646 A2    10/2009

*Primary Examiner* — Tarifur Chowdhury
*Assistant Examiner* — Jonathon Cook
(74) *Attorney, Agent, or Firm* — Luoh J. Wu; Continent Patent Office LLP

(57) ABSTRACT

Apparatus for measuring the distribution of strain and temperature along an optical fibre (34) by analysing the distribution of the Rayleigh scattering and stimulated Brillouin scattering wavelength shifts along the length of a sensing fibre (34) using a Wavelength-Scanning Optical Frequency-Domain Analysis (WS-BOFDA) technique in which a wavelength-swept laser (12) sources a Brillouin "pump" radiation and excites a Brillouin ring laser (14) that sources a Brillouin "stimulus" radiation with wavelength shifted with respect to the excitation of a tuneable quantity. One optical Mach Zehnder or Michelson interferometer (27) is excited by the "stimulus" radiation on both the measurement arm, that comprises the sensing fibre (34), and the reference arm (38) while the "pump" radiation is injected only in the measurement arm by a controllable inhibition system (57). The output of the interferometer (27) is analysed in the frequency domain differential detectors (73, 74) sweeping the wavelength of the pump laser (12) and of the wavelength shift of the Brillouin laser (14). The invented apparatus does not require electro-optical modulators, phase-locking, high power optical amplifiers or microwave electronics and overcomes the prior art issues on manufacturing cost, stability, spatial resolution and on separate measurement of strain and temperature on the same sensor.

10 Claims, 6 Drawing Sheets

(51) Int. Cl.
*G01N 21/63* (2006.01)
*H01S 3/30* (2006.01)
*H01S 3/105* (2006.01)

(52) U.S. Cl.
CPC ....... *G01D 5/35303* (2013.01); *G01N 21/636* (2013.01); *H01S 3/105* (2013.01); *H01S 3/302* (2013.01); *G01N 2021/638* (2013.01)

(58) Field of Classification Search
CPC .... G01N 21/636; G01N 21/638; H01S 3/105; H01S 3/302
USPC .................................................. 356/478, 479
See application file for complete search history.

(56) References Cited

U.S. PATENT DOCUMENTS

| | | | |
|---|---|---|---|
| 2011/0228255 A1* | 9/2011 | Li ......................... | G01B 11/18 356/33 |
| 2016/0025524 A1* | 1/2016 | Nikles .................... | G01K 11/32 356/73.1 |

* cited by examiner

APPARATUS FOR INTERROGATING DISTRIBUTED OPTICAL FIBRE SENSORS USING A STIMULATED BRILLOUIN SCATTERING OPTICAL FREQUENCY-DOMAIN INTERFEROMETER

TECHNICAL FIELD OF THE INVENTION

The present invention concerns an apparatus intended to interrogate a distributed optical fibre sensor by means of frequency-domain analysis of the output signal of an optical interferometer that is excited by a first type of wavelength-swept laser source and that comprises the fibre sensor in its measure arm, in a configuration that allows the sensor to be also excited by a second type of laser source that is characterized by a wavelength-shift with respect to the first laser source that produces light amplification (or depletion) by stimulated Brillouin scattering within the sensing fibre.

The "Brillouin effect" is a non-linear scattering phenomenon in which incident photons of light interact with mechanical vibrations of the medium inside which they propagates to get scattered with a wavelength shifted with respect to the original one, in which the wavelength shift is related to the electro-optical characteristics of the same medium and to the physical characteristics, among which mechanical strain and temperature, that can later such characteristics.

Due to the small entity of the Brillouin wavelength shift in conventional optical fibres, measuring such parameter requires techniques sophisticated and expensive to be implemented.

PRIOR ART

1) BOTDR/BOTDA

Are known several Brillouin sensor interrogators based on time-domain analysis of the propagation of light pulses in an optical fibre. The documents JP2001356070 (also disclosed as GB2368638B), GB2243210A, WO9827406A1, WO2007043432A1 JP2011232138A, JP2007240351A, JP2012063146A, EP0887624A2, WO2006001071A1, JP2009080048, JP2009198389, JP2010217029, U.S. Pat. No. 7,283,216 B1 and EP1760424A1 disclose Brillouin Optical Time-Domain Reflectometers (BOTDR) that combine the time domain reflectometry principle with techniques capable to determine the wavelength shift of the back-scattered photons in a sensing optical fibre due to spontaneous Brillouin scattering effects.

The documents WO2012156978A1, WO2012084040A1, WO2007086357A1, JP2007033183, JP10048065, FR2710150, JP4077641, JP4077641, EP0348235A2, EP1865289A2, EP0348235, DE102008019150A1, JP6273270, JP2010008400A, JP2008286697A, JP2007178346A, US2008068586A1, US2008018903A1, WO2006001071A1 and WO2014155400 disclose Brillouin Optical Time-Domain Analysers (BOTDA) that combine the time domain analysis with stimulated Brillouin scattering between two types of "pump" and "probe" light characterized by a controllable wavelength-shift, in particular the document WO2014155400 discloses the use of a tuneable Brillouin ring laser to produce the wavelength-shifted light. Brillouin interrogators based on time domain analysis are characterized by:

a distance resolution intrinsically limited at ~10 cm due to the minimum life-time of the Brillouin phonon in the non-stationary (pulsed) propagation scheme;

no capability of separating the strain and temperature effects due to their intrinsic combination in contributing to the entity of the Brillouin wavelength shift;

the use of high-speed light intensity modulator(s) (expensive parts) to produce the pulsed propagation that is necessary for the time-domain interrogation;

the use of high-power optical amplifier (expensive part) for the pump light for having an appreciable Brillouin amplification even with the very small interaction time consequent to the pulsed propagation that is necessary for the time-domain interrogation;

the use of one high-speed sampling digitizer (expensive part) for recording the time-varying perturbation on the probe lightwave that allows to reconstruct the distance distribution of the Brillouin amplification (minimum $2 \cdot 10^9$ samples/s for a 10 cm resolution).

2) BOCDA

The document K. Hotate and T. Hasegawa, IEICE Trans. Electron., E83-C, 3 (2000) discloses a Brillouin sensor interrogator based on Optical Correlation-Domain Analysis (BOCDA) according to the schematic in the frame 2 of the FIG. 1, where frequency-modulation is applied to both probe and pump light by means of Alternate Current (AC) superimposition to the bias current of a Distributed Feed-Back laser Diode (DFB-LD). Such modulation controls the position along the sensing fibre at which the Brillouin amplification can occur due to the matching of the optical correlation between the two modulated pump and probe lightwaves. In the BOCDA the light propagation and Brillouin scattering in the sensor are stationary in time and space, that allows to overcome the large distance resolution limit of non-stationary time-domain interrogation schemes (BOCDA resolution down to 1.6 mm have been reported). BOCDA is necessarily characterized by:

limitation of the sensor length (maximum range of 1 km has been reported) due to the practical feasibility limits of the frequency modulation of the laser source;

no capability of separating the strain and temperature effects due to their intrinsic combination in contributing to the entity of the Brillouin wavelength shift;

the use of multiple light intensity modulators (expensive components) to produce the wavelength-shift required for stimulated Brillouin amplification and for controlling the position of the correlation peak;

the use of expensive power optical amplifier (expensive component) for the pump light.

Known BOCDA embodiments are also characterized by:

a non-swept DFB-LD laser source that can be frequency modulated within few MHz around the centre frequency but that is not suitable for being swept over a much broader (i.e. 20 nm) wavelength interval;

not comprising any interferometer neither in the sensor path nor in the general layout; and p1 the generation of the wavelength-shifted Brillouin probe by means of optical side-band modulation technique involving the use of expensive parts such as high-speed nested electro-optical modulator and microwave synthesizer and amplifiers.

3) Rayleigh-OFDR

Several documents (i.e.: M. K. Bamoski and S. M. Jensen—"Fiber waveguides: A Novel Technique for Investigating of Attenuation Characteristics", Appl. Opt., vol. 16, pp. 2112-2115, 1978) disclose Frequency (or Wavelength) Scanning Optical Frequency-Domain Reflectometers (FS-OFDR or WS-OFDR) that can be ascribed to the schematic in the frame 1 of the FIG. 1. The OFDR comprises an optical interferometer in which the sensing fibre is part of the measurement arm, and that is excited by a wavelength-swept coherent light source. Each single propagation discontinuity in the measurement arm (i.e. Rayleigh sensing and Fresnel reflections sources for a backreflection sensing scheme like the one illustrated) produces an individual output signal contribution by interfering with the signal of the reference arm, the intensity of which arises form the interference condition that is on the wavelength of the excitation source and on the relative position of the specific discontinuity that generates the signal on the measurement arm with respect to the length of the reference arm. By linearly sweeping the wavelength of the excitation source the intensity of each single output signal contribution results sine-modulated with a frequency that depends on the location of the discontinuity source, thus, by Fourier transforming the signal into the frequency domain each single discontinuity (and its intensity) can be individually identified with a single frequency spectral line of the signal (and its intensity).

OFDR distance resolution $\Delta z$ depends on the width of the wavelength sweeping interval that is swept by the excitation source according to the relation $\Delta z \approx c \lambda^2/(2 n_g \Delta \lambda)$ in which c is the speed of the light, $n_g$ is the group refractive index, $\lambda$ is the average wavelength of the excitation light and $\Delta \lambda$ is the wavelength sweeping width (40 nm sweeping width achieves 20 μm resolution), furthermore the information content of the output signal is produced by optical interference phenomena, a condition that allows the use of coherent detection techniques having sensitivity and signal/noise performance much better than those achievable in time-domain, correlation-domain and modulation-transfer techniques. It is also known the use of OFDR for distributed strain and temperature sensing by means of the evaluation of Rayleigh wavelength shift.

OFDR is necessarily characterized by:
no capability of separating the strain and temperature effects due to their intrinsic combination in contributing to the entity of the Rayleigh wavelength shift (similarly to what happens for Brillouin shift);
intrinsic limitations of the Rayleigh-shift technique in the measurement of large strain (temperature) changes due to the difficulties in recognizing large changes in the pattern of Rayleigh reflection sources;
Known OFDR embodiments are also characterized by:
using Rayleigh scattering sources (and not being capable to selectively detect and recognize Brillouin scattering sources);
not inducing stimulated Brillouin scattering neither in the sensor path nor in the general layout for the use in the OFDR.

4) Modulation-transfer BOFDA (Improper BOFDA)

The documents Garus D. et al. "Brillouin Optical-Fiber Frequency-Domain Analysis for Distributed Temperature and Strain Measurements", J. of Lightwave Techn., Vol. 15, No. 4 (April 1997) [D1], DE19950880 [D2], EP2110646A2 [D3] and Kasinatan M. et al. "Analysis of Stimulated Brillouin Scattering Characteristics in Frequency Domain", Int. Conf. on Optics and Photonics (ICOP 2009, Chandigarh, India, Nov. 1, 2009) [D4], all disclose variants of a same device that is improperly-named Brillouin sensor interrogator based on Optical Frequency-Domain Analysis (BOFDA). The working scheme of this device is sketched in the frame 3 of the FIG. 1, and is characterized by the fact that the Brillouin pump is intensity-modulated by a modulation signal containing various frequency components (from 10 kHz to 20 MHz reported) by means of an electro-optical intensity modulator and is then injected in the sensing fibre in counter-propagation with a Continuous Wave (CW) non-modulated Brillouin probe. At the sensor locations where the strain- and temperature-dependant Brillouin wavelength shift matches the actual wavelength shift between the pump and the probe, Brillouin amplification occurs and transfers the intensity modulation from the pump to the probe, but with a phase delay with respect to the injected pump modulation that depends on the modulation frequency and on the position along the sensor where the modulation transfer happens. The probe signal containing the transferred modulation is then analysed in the frequency-domain after Fast Fourier Transforming (FFT) and the phase and amplitude transfer function with respect to the modulating signal is exploited in order to reconstruct the position dependence of the Brillouin-induced modulation-transfer along the sensor fibre. In such sensor interrogation scheme the light propagation is stationary in time and space, that allows to overcome the distance resolution limit of time-domain interrogation schemes. However, in the modulation-transfer BOFDA the information content of the perturbed probe is derived from a local transfer process of the pump modulation and not from local optical interference phenomena like it happens in the real Optical Frequency-Domain Reflectometers (OFDR, that will be described in the following) and for this reason the system has to be considered and improper BOFDA.

The document [D1] discloses a first variant of the modulation-transfer BOFDA where is used a conventional Optical Phase-Locked Loop (O-PLL) technique between two separate Nd:YAG tuneable lasers in order to produce the pump and probe with the desired wavelength-shift. It has to be noted that the "tuneability" of the lasers (pag. 655, left column, first row) is only used to achieve a controlled wavelength shift between the two lasers (pag. 655, left column, rows 5-7) by means of a feedback loop fed by their heterodyne signal (pag. 660, FIG. 9). The disclosed solution uses Nd:YAG lasers that are not suitable for producing a wavelength swept signal due to the slow and non-linear tuning mechanism and that are characterized by a tuneability limited to only 0.4 nm (=120 GHz, Koechner W., Solid-State Ingegneria Laser, $2^{nd}$ Ed., Springer-Verlag, 1998). The use of the tuneable source for providing a wavelength-swept excitation is neither disclosed nor suggested in the documents as well as any idea by itself of wavelength-sweeping any of the laser sources, for this reason nothing in the prior art discloses, hits or makes obvious the use of a wavelength-swept laser excitation source.

The document [D4] discloses a second variant of the modulation-transfer BOFDA where a conventional optical side-band modulation technique is used to generate the wavelength-shifted probe signal from a fraction of the output of the same fixed-wavelength DFB laser that sources the pump signal, using a second expensive optical modulator. This provides a further clue that the tuneability of the Nd:YAG source cited in the other paper represents only an incidental condition and is out of the scope of the modulation-transfer BOFDA sensing mechanism and that nothing in the prior art discloses, hits or makes obvious the use of a wavelength-swept laser excitation source.

Furthermore no prior art discloses, suggests, makes obvious or even simply imaginable the use of an optical interferometer (in particular Michelson-type or Mach-Zehnder type, with classical or modified topology) for the scope of resolving the distance distribution of stimulated Brillouin amplification in the sensor, and in particular for generating an interference signal between two fractions of the same excitation lightwave only one of which is amplified (or attenuated) at some sensor locations by stimulated Brillouin interaction. The only interferometer cited ([D1], pag. 655, left column, line 9) is a Fabry-Perot tunable filter in a setup for Brillouin linewidth measurement (pag. 655, FIG. 1) that is out of the scope of the Brillouin distributed sensing and that is not configured to have Brillouin amplification in any of its light interference paths.

Similarly, no prior art discloses, suggests, makes obvious or even simply imaginable the use of a coherent detection technique for selectively detect the unbalancing of an optical interferometer by means of a balanced differential photodetector, where the said unbalancing arises by the occurrence of Brillouin amplification in the measurement arm that comprises the sensing fibre of an interferometer.

The known modulation-transfer BOFDA require one [D1] or even two [D4] optical intensity modulators (expensive parts).

Due to practical feasibility reasons, however, the improper-BOFDA is necessarily characterized by:
  limitation of the distance resolution (maximum resolution of 5 cm has been reported) due to the difficulties of compensating for the non-linear behaviour of the optical modulator;
  no capability of separating the strain and temperature effects due to their intrinsic combination in contributing to the entity of the Brillouin wavelength shift;
  the use of at least one light intensity modulator (expensive component) to introduce the pump modulation;
  the use of one medium-speed sampling digitizer (relatively expensive part) for digitizing the modulated lightwave at least twice of its highest frequency content (Nyquist frequency limit).

Known improper-BOFDA embodiments are also characterized by:
  the use of non-swept laser sources for both the pump and probe signal;
  not comprising any interferometer neither in the sensor path nor in the general layout; and
  neither using nor being capable to take advantage from coherent optical detection and not being suitable for using balanced differential photodetectors to be connected at the differential output ports of a Mach-Zehnder or Michelson interferometer, either in a traditional or modified topology.

5) Wavelength-division Multiplexed OFDR+BOTDA Hybrid

The document Zhou D. et al., "Distributed Temperature and Strain Discrimination with Stimulated Brillouin Scattering and Rayleigh Backscatter in an Optical Fiber", Sensors 2013, 13, 1836-1845 discloses an hybrid OFDR+BOTDA solution according to the schematic in the frame 4 of the FIG. 1, in which the same sensing fibre can be interrogated by a known OFDR apparatus operating in the "C band" (1531÷1570 nm) and by a known BOTDA apparatus operating at 1310 nm by means of a conventional Wavelength-Division Multiplexing (WDM) technique. The said hybrid solution has the scope of decoupling the effect of the strain and of the temperature by means of solving the system of equation that is obtained by measuring the distribution of Rayleigh wavelength shift and the distribution of Brillouin frequency shift. Such known hybrid OFDR+BOTDA embodiment is characterized by:
  using separate OFDR and BOTDA that share the same sensing fibre by means of WDM, thus multiplying the cost of the equipment;
  using a time-domain technique for the Brillouin sensor interrogation that retains all its typical limitations.

SCOPE OF THE INVENTION

The main scope of the present invention is that of achieving an apparatus for interrogating optical fibre sensors based on the stimulated Brillouin scattering that could overcome the distance resolution performance limitation and that could break down the level of cost of the known devices.

Secondary (I) scope of the present invention is that of achieving an apparatus capable of Brillouin distributed sensor interrogation in which, in order to reconstruct the distance distribution of the Brillouin amplification effect, it is employed a properly said optical interferometer suitable for outputting a signal suitable for coherent optical detection and balanced differential photodetector demodulation.

A further (II) secondary scope of the present invention is that of achieving an apparatus capable of Brillouin distributed sensor interrogation using a CW (non-pulsed) propagation scheme in which it is not use any optical modulator component.

A further secondary (III) scope of the present invention is that of achieving an apparatus capable of both Brillouin-shift and Rayleigh-shift distributed sensor interrogation by means of switching the configuration of the same set of components.

A further (IV) secondary scope of the present invention is that of achieving an apparatus capable of Wavelength-Scanning Brillouin Optical Frequency-Domain distributed sensor interrogation using a technical solution to generate the Brillouin pump and probe lightwaves capable to overcome the limitations of other known solutions (O-PLL and O-SSB) in terms of industrial cost, critical tuning, technical complexity, stability and reliability.

A further secondary scope (V) of the present invention is that of achieving a wavelength-agile apparatus capable of Brillouin distributed sensor interrogation that is capable to maintain the required wavelength shift between Brillouin pump and probe signal without the need of complex and sophisticated adjustments of the operating parameters with the changes of the wavelength.

DISCLOSURE OF THE INVENTION

In a first broad independent aspect the present invention provides a Wavelength-Scanning Brillouin Optical Frequency Domain Analyser (WS-BOFDA) apparatus comprising:
  a1) a wavelength-swept primary source of coherent light; and
  a2) a secondary wavelength-shifted source of coherent light, having instant-by-instant a wavelength shift controllable and known with respect to the wavelength of the primary source during the wavelength-sweeping process; and
  a3) an optical interferometer in which the excitation light, supplied by a first one of the above mentioned sources, is split into the measurement arm, comprising the sensing fibre, and into the reference arm; and it is then recombined to produce an optical interference signal; and
  a4) means to route the light supplied by the second one of the mentioned sources into the measurement arm of the said interferometer in order to produce local Brillouin amplification (or attenuation) at any sensor location at which the current wavelength shift falls within the local temperature and strain dependent Brillouin gain band;

a5) means to measure the interference signal at the differential outputs of the interferometer with a balanced differential photodetector; and a6) means to detect and analyse the measured interference signal in the frequency domain with respect to the value of the wavelength-swept interferometer excitation and at different values of the wavelength shift between the two sources.

Due to the interference between the fraction of excitation signal that arrives unperturbed from the reference arm of the interferometer and the fraction that arrives amplified by local Brillouin effects in the measurement arm, any Brillouin amplification source along the sensor will contribute to the total output signal intensity depending on its location (path length) and on the excitation wavelength, so that, when the excitation wavelength is swept, each single intensity contribution will periodically vary with a frequency that depends on the source location along the sensor, and by analysing the total output signal in the frequency domain, i.e. by Fast Fourier Transforming (FFT), each amplification source is easily identified and resolved as a specific frequency component. By varying also the wavelength shift between the two sources, sensor locations performing as Brillouin amplification sources at different conditions of temperature and strain are then detected and recognized.

The technical effects of the introduced innovations are:

b1) the combination of the points a1), a3) and a6) provides the capability of resolving the distance distribution of the amplification (or attenuation) sources by means of wavelength-scanning optical frequency-domain interferometry and without the use of any expensive optical modulator component; and b2) the combination of the points a2), a4) and a6) provides the capability of inducing local Brillouin amplification (or attenuation) sources in the sensing fibre according to a CW propagation scheme requiring reduced Brillouin pump power (thus avoiding the need of expensive optical power amplifiers) and it also provides the capability of locating the Brillouin peak frequency shift in the sensor by interpolating the gain measurements at different wavelength shifts between the two sources; and b3) the combination of the points a5) and a3) provides the capability of selectively detect and distinguish the unbalancing of the interference signal that is due to the presence of amplification (or attenuation) sources in the sensing fibre allowing thus to distinguish the wanted information from other noise sources that are necessarily present due to the sensor interrogation scheme (in particular that from the light injected in the measurement arm only that produces a common mode signal at the outputs of the interferometer, directly or indirectly by Rayleigh backscattering according to the propagation scheme);

This unique combination of features provides a solution for the main scope and for the secondary scopes (I) and (II) that is not only novel but also characterized by a combination of substantial innovations (points from a1) to a5)) that, are not suggested, hinted, made obvious or simply imaginable for a technician with experience in the field of Brillouin sensing considering the known prior art.

In a first subsidiary aspect the present invention provides a solution capable of both Brillouin-shift and Rayleigh-shift distributed sensor interrogation according to the secondary scope (III) by means of an optic switch (or variable attenuator) configured to control the routing of the excitation of the interferometer and of the Brillouin interacting lightwaves, so that the same Wavelength-Scanning Optical Frequency-Domain Analyser can be switched between a "Brillouin mode" in which both Brillouin pump and probe lightwaves are injected in the sensor in order to generate local Brillouin interactions, and a "Rayleigh-mode" in which both arms of the interferometer are excited only by fractions of the same lightwave in a configuration capable to measure the distribution of local Rayleigh scattering sources. The technical effect of this further innovation is the capability of performing both Brillouin and Rayleigh-shift distributed measurements and separate the contributions of temperature and strain in the same sensor, with a solution that, by allowing to use the same hardware for both scopes, is more cost effective and space-saving.

In a second subsidiary aspect the present invention provides a Wavelength-Scanning Brillouin Optical Frequency-Domain distributed using a Brillouin ring laser in order to generate a wavelength-shifted signal suitable to perform as Brillouin probe, with a wavelength shift that is intrinsically locked to the pump light source in particular remaining constant and locked instant-by-instant during the wavelength-sweeping process of the primary source, and where the said wavelength-shift is also easily tuneable in order to allow the Brillouin frequency analysis required by the distributed sensing scope. The technical effect of this further innovation is the capability of overcoming the limitations of other known solutions (O-PLL and O-SSB) in terms of industrial cost, critical tuning, technical complexity, stability and reliability according to the secondary scope (IV) and to provide a solution for sourcing the wavelength-shifted pump and probe signal that is compatible with a wavelength-swept interferometer excitation process such as required for the WS-BOFDR scope, in particular according to the secondary scope (V).

In further subsidiary aspects, the present invention may also comprise:

reflector or absorber mean(s), possibly having partial reflection/absorbance characteristics fixed or variable, suitable for inducing a stationary lightwave propagation in the sensing arm of the interferometer;

system(s) for suppressing the mode-hopping in the Brillouin ring laser such as a mode mixer, active or passive, or a system capable to change the resonance length of the cavity of the Brillouin ring laser so that to tune it continuously during the wavelength-seeping of the primary laser source;

system(s) for purging the spectrum of the Brillouin ring laser, such as means to interrupt the laser ring feedback or to change the optical gain of the cavity or change its optical attenuation so that to suppress the drift and hysteresis of the Brillouin ring laser that are related to the wavelength sweeping process;

mean(s) to control and stabilize the strain and/or temperature of the Brillouin gain medium of the Brillouin ring laser, i.e. by means of a feedback control system comprising also sensors of strain and/or temperature;

mean(s) to control the polarization such as for example a polarizer or a polarization controller in any of the arms of the interferometer or in any of the light injection arms;

polarization-sensitive photodetector mean(s) in the detector and analyser system;

mean(s) to generate optical pulses in order to limit the time of interaction of the Brillouin pump and probe in the measurement arm i.e. with the scope of extending the measurement range by limiting the area of pump depletion;

light waveguide(s) having enhanced Brillouin gain such as a Photonic Crystal Fibre (PCF), a silicon photonics waveguide, an optical fibre having reduced mode field diameter, a Telluride and/or chalcogenide and/or Bismuth-glass optical fibre, a non-linear optical fibre having an optimized overlapping between the longitudinal modes optical and acoustical, also possibly connected with multiple different waveguide sections;

mean(s) of optical amplification such as Erbium-doped fibre amplifier, Semiconductor Optical Amplifier, Raman amplifier, Brillouin amplifier;

mean(s) of variable optical attenuation;

mean(s) to change the length of the reference arm of the interferometer such as an external changeable patch cable or optical switch, so that to allow an usable sensing length exceeding the coherence length of the laser sources that excites the interferometer;

auxiliary interferometer(s), having a constant arm length unbalancing and suitable for measuring the wavelength-sweeping speed of the primary source in order to linearize the data acquisition during the sweeping process;

wavelength reference(s) such as HCN atomic absorption cell, and/or interference ethalon comb generator and/or Bragg reflector for calibrating the wavelength sweeping process.

DETAILED DESCRIPTION OF THE PREFERRED EMBODIMENTS

Figure 1:
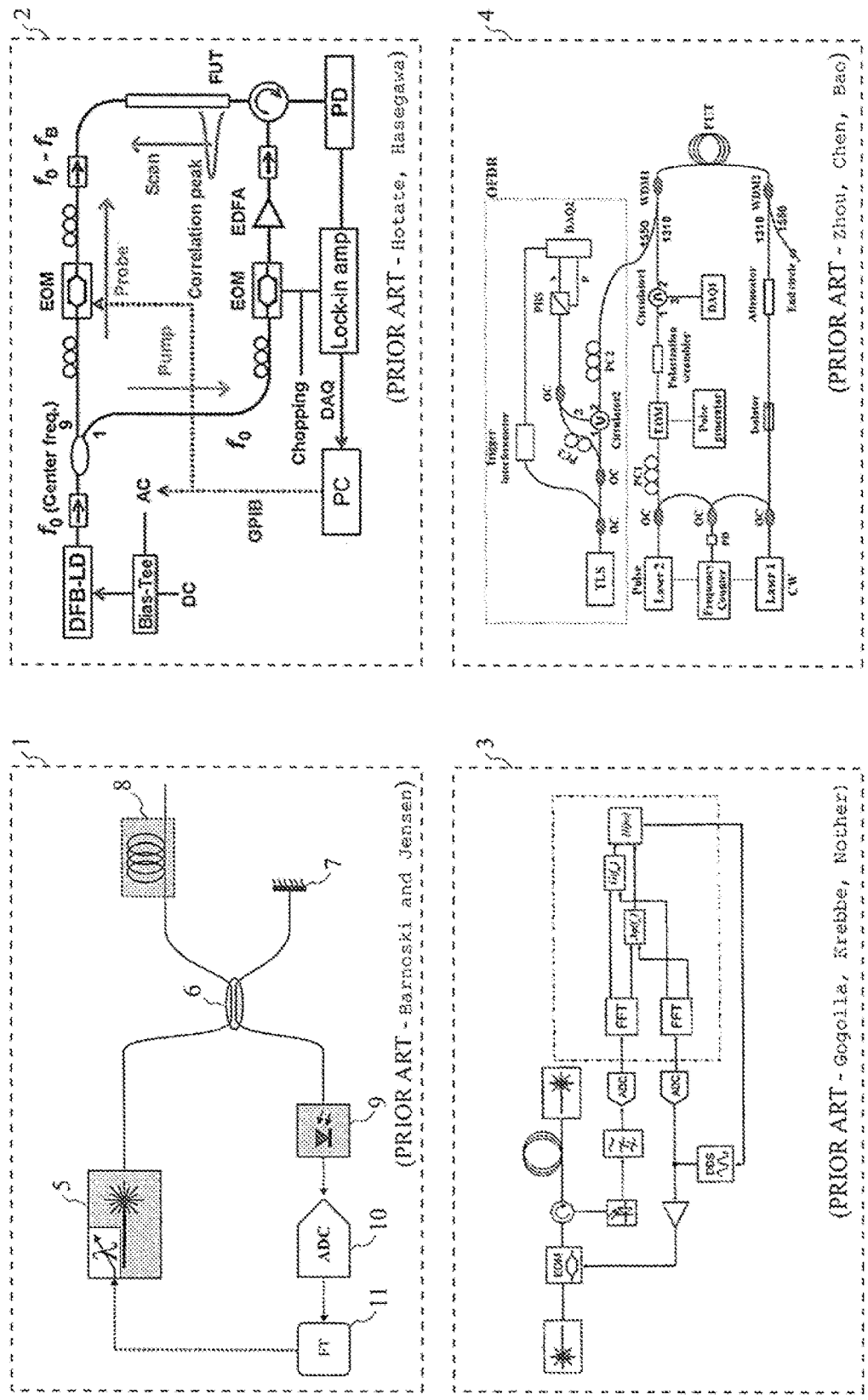
FIG. 1 illustrates the relevant prior art.
Figure 2:
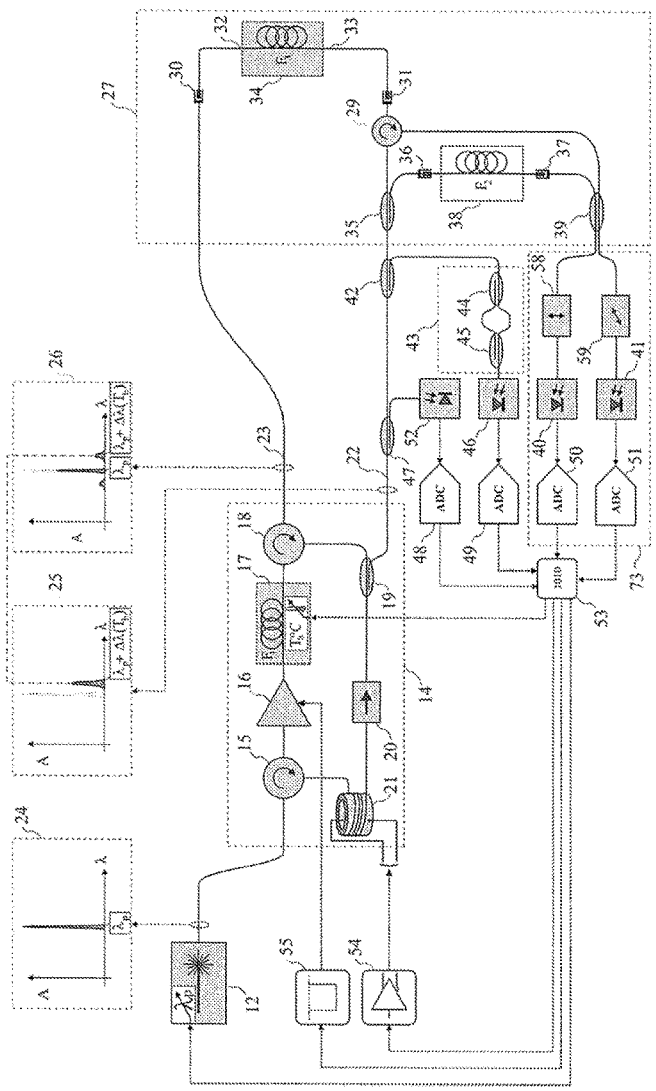
FIG. 2 illustrates a first preferred embodiment of the present invention according to the transmission-type configuration.

A full and enabling disclosure of the present invention, including the best mode thereof, directed to one of ordinary skill in the art, is set forth in the specifications, which makes reference to the appended figures, in which:

The FIG. 2 discloses a partial schematic representation, non-limiting, of an embodiment of an apparatus according to the present invention in which the sensing fibre (34) is connected in a transmission-type configuration.

The apparatus comprises a primary laser (12) that sources a monochromatic light of wavelength $\lambda_P$, sweepable and having a spectrum as illustrated in the frame (24), with linewidth smaller that the Brillouin gain bandwidth in the sensing fibre (that is suitable to perform as stimulated Brillouin pump or probe).

The said light seeds a Brillouin ring laser optical circuit (14) by means of a circulator (15) and, after having been amplified by an optical gain block (16), preferentially bi-directional, is injected in a Brillouin gain medium waveguide that is kept in uniform and controllable conditions of strain and temperature $T_b$. In the gain medium the seed light generates backward and forward Brillouin scattering. The depleted seed light, the spectrum of which (26) also comprises the weak forward Stokes and anti-Stokes Brillouin scattering components, is picked-up by the circulator (18) after the gain medium (17) and routed in the fibre (23) to be injected at the first end (32) of the sensing fibre (34) that is connected to the apparatus through the connector (30).

The Brillouin stokes backscattering in the gain medium (17) is also amplified by the gain block (16) and is routed by the circulator (15) into the closing arm (14) of the ring circuit to inject it in counter-propagation with the seed that acts as the Brillouin pump. The closing arm (14) also comprises a piezoelectric fibre stretcher consisting of a length of fibre coiled on a piezo-electric element (21) having the function of stretching/shortening the length according to the voltage applied to the same element. The closing arm (14) could also comprise an optical isolator (20) to impose a single allowed direction for the light propagation in the same closing arm (14) that is in accordance with the Brillouin back-propagation direction in the gain medium (17). The said isolator (20) is in general preferred when the circulator(s) (15) and/or (20) are replaced by a different type of routing mean(s) such as for example directional coupler(s).

The ring circuit (14) constitutes a Brillouin ring laser with an output spectrum (25) where dominates the backward Brillouin stokes line having wavelength $\lambda_P + \Delta\lambda(T_b)$ (that is wavelength-shifted with respect to the seed of a quantity $\Delta\lambda$ that is controlled by the temperature of the gain medium. The Brillouin ring laser spectrum is suitable for acting as Brillouin probe light in cooperation with the (depleted) seed used as Brillouin pump.

Part of the backward Brillouin stokes light is picked-up by the coupler (19) and routed into the arm (22) in order to perform as the excitation light for the sensing interferometer (27) that could however have a configuration different from the Mach-Zehnder configuration that is illustrated. The excitation light injected in the sensing interferometer (27) is divided by a splitter (35) that injects part of it into the measurement arm that comprises the sensing fibre (34) and the remaining part into the reference arm constituted by the fiber optic (38), possibly interchangeable by acting on the optical connectors (36, 37). In particular, in the scheme depicted, the excitation light is injected at the sensor end (33) that is connected to the apparatus though the optical connector (31) in counter-propagation with the depleted seed light that is injected at the opposite sensor end (32).

The light perturbed by Brillouin amplification in the sensing fibre (34) is picked-up by the circulator (29) and routed to the combiner (39) where it interferes with the light coming from the reference arm (38). The differential interference outputs produced by the splitter (39) are then analyzed by a photodetector taking advantage of their differential characteristic though a balanced differential pair of detectors (40, 41), possibly sensitive to the polarization of the light, in order to be digitized and then analysed by the control unit (53).

Possibly, a small part of the ring laser output can be picked-up from the fibre (22) though a coupler (47) for surveying the output power of the ring laser through the detector (52) and digitizer (48) and feedback consequently the piezoelectric stretcher (21) through a control system (53) and a power amplifier (54) with the scope of tuning the length of the resonant cavity of the ring laser (14) following the wavelength sweeping of the primary seed laser (12), so that to suppress the mode-hopping that could be present in the ring laser with the continuously changing output wavelength. Such mode-hopping suppression can be also achieved by means different from the one that is illustrated such as for example by introducing a mode mixer in the ring circuit (14) that could be for example constituted by a section of multi-mode fibre connected in the single-mode circuit possibly with tapered splices, or a free-space propagation section between two collimators introduced in the same ring (14).

Possibly, a fraction of the excitation light of the interferometer can be also picked up i.e. through the coupler (42) to excite an auxiliary interferometer (43) used to linearise the wavelength sweep. This said auxiliary interferometer, that can be also arranged in a configuration different from the one (Mach-Zehnder) illustrated, is characterized by measurement and reference arms of fixed length so that to produce an interference output that is function of the wavelength sweep of excitation. The said output is routed to the photodetector (46), digitized (49) and used by the control unit (53) to linearise the wavelength-sweep that the same control unit (53) imposes to the primary source (12).

the control system (53) can also drive a purge system for the output spectrum of the Brillouin ring laser (14) for example by means of an inhibition pulse (55) for the optical gain block (16) in the laser ring or acting on means to introduce optical attenuation or interruption of the ring, or also by means of a transitory inhibition of the seed light.

The reference arm (38) of the sensing interferometer might also comprise a variety of fibre segments and optical switch(es) or multiplexer(s) capable to change the length of the same arm.

The control system (53) is configured to perform the following sequence of operations:
  a. select a first value of the wavelength shift between the seed and ring laser outputs;
  b. start a wavelength sweep of the seed source;
  c. if required, adjust instant-by-instant the cavity length of the ring laser;
  d. record the output of the sensing interferometer;
  e. any new fringe detected from the auxiliary interferometer repeat the operations c) to d);
  f. repeat the operations from c) to e) until the width of the wavelength sweep reaches a value that allows to achieve the desired distance resolution (typically 40 nm sweep for 20 µm resolution);
  g. analyse the recorded output of the sensing interferometer in the frequency domain with respect to the wavelength sweep in order to reconstruct the distribution of Brillouin amplification sources along the sensor
  h. select a different value of the wavelength shift between the seed and ring laser output;
  i. repeat the operations from b) to h) until the desired measurement interval is covered;
  j. perform an Lorenz interpolation of the Brillouin gain spectrum for each measurement distance point and identify the Brillouin peak gain frequency;
  k. evaluate and make available the distribution of the Brillouin peak gain frequency with respect to the position along the sensor.

Figure 3:
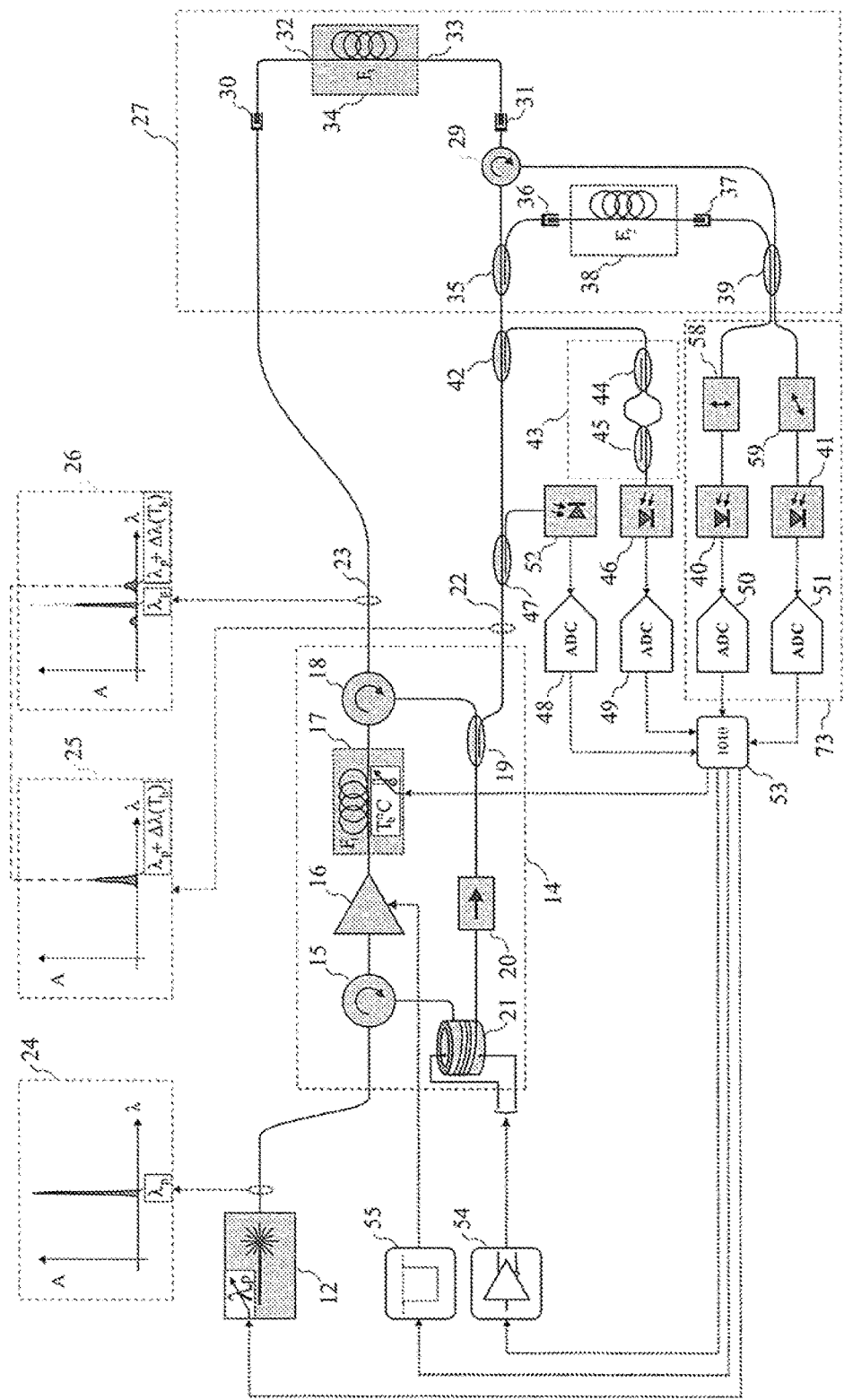
FIG. 3 illustrates a second preferred embodiment of the present invention according to the transmission-type configuration.

The FIG. 3 discloses a schematic representation, non-limiting, of different embodiment of the apparatus according to the present invention characterized by a "transmission-type" connection of the sensing fibre analogous to the one illustrated in FIG. 2. The scheme of FIG. 3 is characterized by a different and more simple configuration of the Brillouin ring laser (14) that does not comprise means to pick-up the depleted seed light. In the scheme of FIG. 3 the counter-propagation of Brillouin pump and probe signals in the sensor (34) is obtained by injecting at one end (33) the output of the Brillouin ring laser and at the opposite end (32) part of the light sourced by the seed laser (12) and picked-up by a coupler (12) before the Brillouin ring laser.

Figure 4:
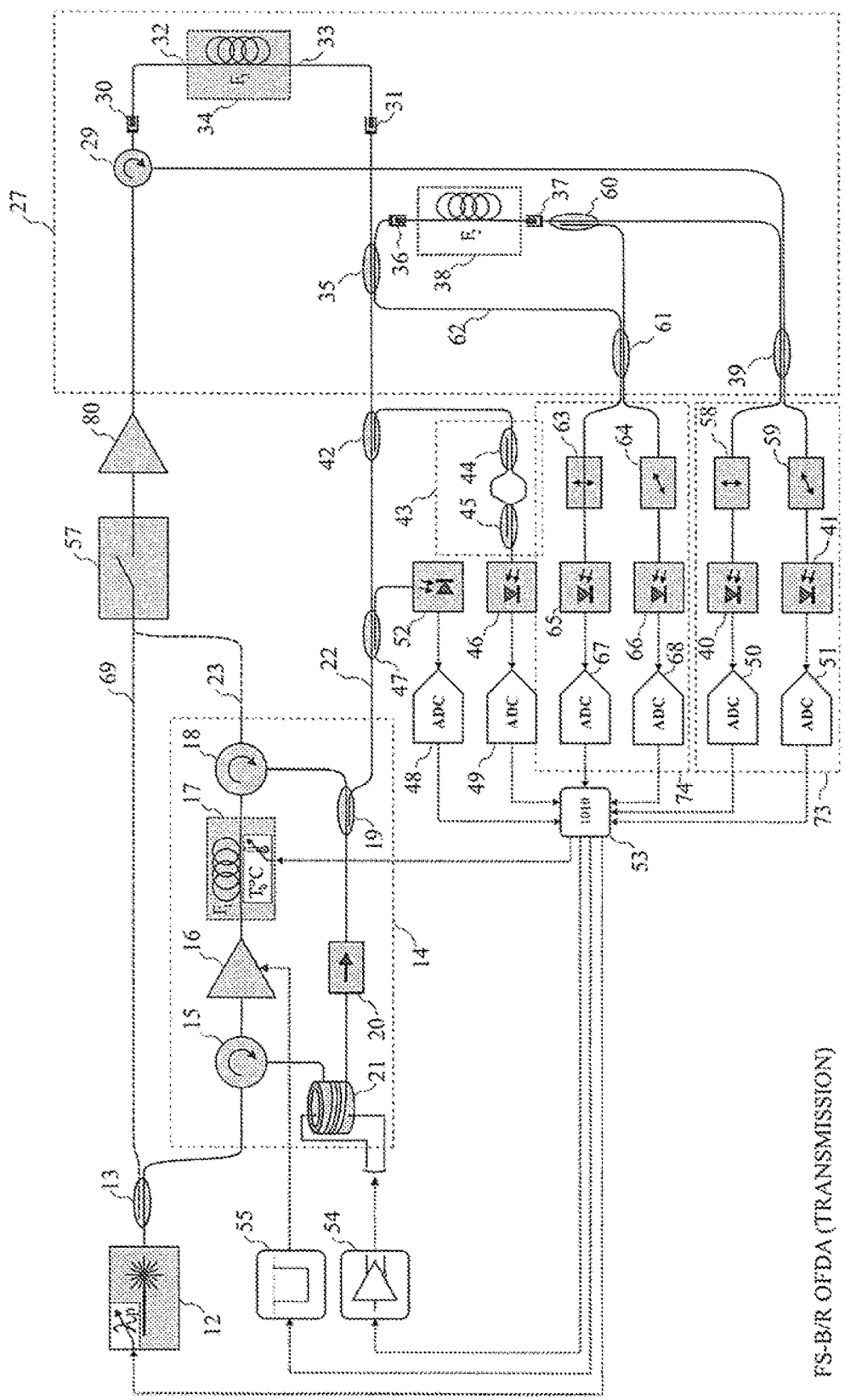
FIG. 4 illustrates a third preferred embodiment of the present invention.

The FIG. 4 discloses a schematic representation, non-limiting, of an enhanced embodiment of the apparatus according to the present invention characterized by the additional presence of the optical switch (57) capable to disable the injection of the light at the end (32) of the sensor, and are also present additional balanced detector means (74) to measure the differential interference signal with a balanced differential photodetector between the fraction of the excitation signal reflected along the measurement arm (34) and the fraction transmitted through the reference arm (38); while the other first balanced detector means (73) measures the differential interference signal between the fraction of the excitation signal perturbed by the local Brillouin amplification and transmitted along the measurement arm (34) and the fraction transmitted through the reference arm (38).

The apparatus according to FIG. 4 works as a WS-BOFDA when the optical switch (57) is closed, similarly to what is disclosed in the FIGS. 2 and 3. When the switch (57) is opened, for example controlled by the control unit (53), the apparatus works as an OFDR by analysing the information collected by the detector group (74) in the frequency-domain with respect to the wavelength sweep and keeping constant the wavelength shift of the Brillouin ring laser. Thank to such mode switching capability the apparatus of FIG. 4 can measure both the distribution of the Brillouin peak frequency along the sensing fibre (WS-BOFDA mode) and the distribution of the Rayleigh wavelength shift along the sensing fibre (OFDR mode) and, considering that the dependence of the Brillouin and Rayleigh shifts from temperature and strain are different and known constants, the distributed measurement of temperature and strain separately obtained. The apparatus of FIG. 4 can also be obtained according to the variants disclosed in the FIGS. 2 and 3.

Figure 5:
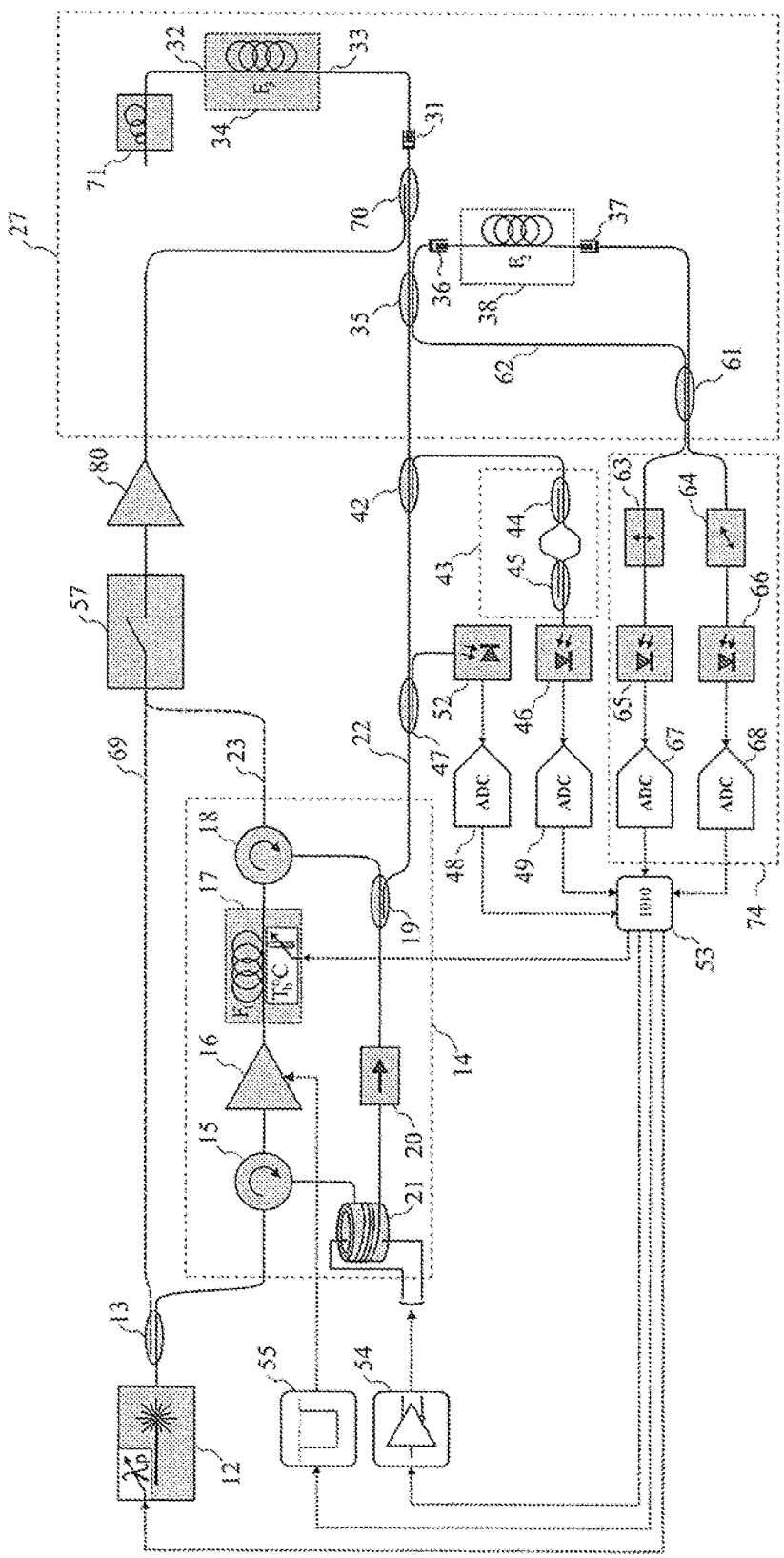
FIG. 5 illustrates a fourth preferred embodiment of the present invention.

The FIG. 5 discloses a schematic representation, non-limiting, of an further embodiment of the apparatus according to the present invention also having the switchable WS-BOFDA/OFDR analysis mode capability and that is characterized by the fact that both the pump and the probe signal are injected from the same end (33) of the sensing fibre (34) that constitutes the measurement arm of the interferometer (27) that is illustrated in an hybrid configuration in which the balanced detector group (74) receives the interference signal between the back-scattered light in the measurement arm (34) and the transmitted light along the reference arm (38).

At the opposite end (32) of the sensor (34) it could be present an optical reflector or absorber (71), possibly partial, to create a stationary or non-stationary lightwave propagation in the sensor. The apparatus of FIG. 5 can also be obtained according to the variants disclosed in the FIGS. 2 and 3.

Figure 6:
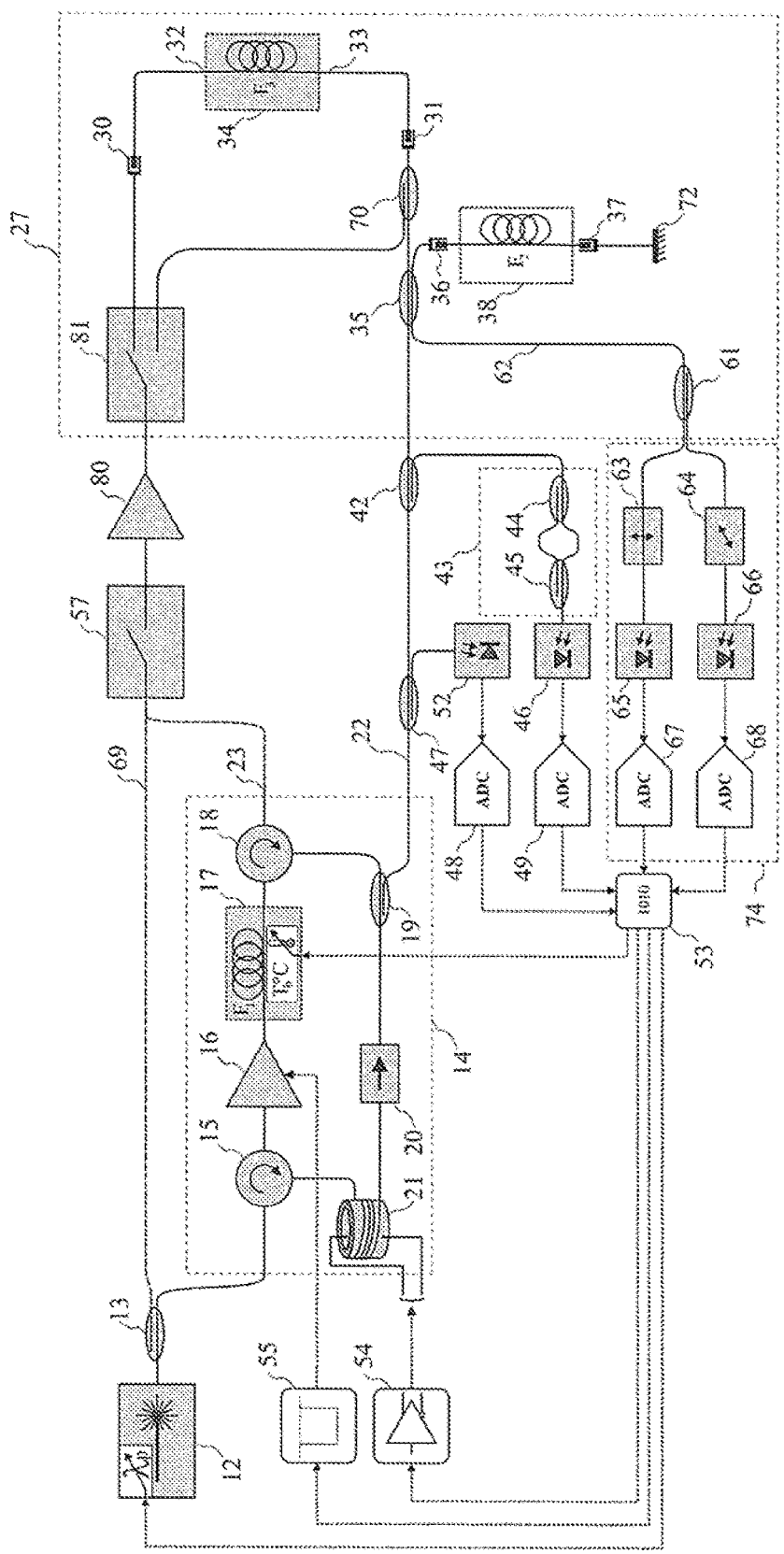
FIG. 6 illustrates a fifth preferred embodiment of the present invention in which the interferometer is arranged according to Michelson configuration.

The FIG. 6 discloses a schematic representation, non-limiting, of an further embodiment of the apparatus according to the present invention characterized by a Michelson-type configuration of the sensing interferometer (27) in which the detector (74) receives the interference signal between the light back reflected by the Brillouin (or Rayleigh) sources along the measurement arm (34) and the light backreflected by a mirror (72) at the end of the reference arm (38). In such configuration the coupler (35) acts both as splitter and re-combiner. An optical switch (81) can be also present to switch between a mode in which the sensor is connected in a transmission configuration and a mode in which the sensor is connected in a reflection configuration. This last said switching capability can be also introduced in the other variants of the apparatus according to the present invention.

It is also made clear that in any variant of the apparatus according to the present invention it could be possible to choose the excitation source of the sensing interferometer between the seed laser and the Brillouin ring laser so that to obtain measurement configurations where the unbalancing of the interferometer is due by Brillouin amplification of a Stokes probe signal, or by Brillouin attenuation of an anti-Stokes probe signal, or by depletion or enrichment of the pump signal.

It is also made clear that modifications and variations can be made to the described device without leaving the scope of protection of the present invention.

What is claimed is:

1. An apparatus for interrogating at least one sensing optical fibre (34) by analysing the distribution of the peak frequency-shift of stimulated Brillouin scattering along the length of the sensing fibre (34) using a wavelength-scanning optical frequency-domain interferometric technique and characterized by the facts of comprising:
    at least one wavelength-swept primary source (12) of radiation characterized by a wavelength $\lambda P$, and by a spectral linewidth not greater than the spectral width of the Brillouin scattering in the sensing fibre (34) and characterized by a wavelength sweeping width of various nm or in any case big enough to achieve the desired resolution $\Delta z$ according to the $\Delta z \approx c \lambda^2/(2 n_g \Delta \lambda)$; and
    at least one secondary source (14) of wavelength $\lambda_P + \Delta \lambda$ instant-by-instant shifted with respect to the sweeping wavelength of the primary source $\Delta_P$ of a quantity $\Delta \lambda$ that is constant during the wavelength sweeping process and that can be arbitrarily controlled within the limits required for the desired Brillouin analysis scope; and
    at least one sensing optical interferometer (27), having ordinary or modified Mach-Zehnder or Michelson topology, that is excited by one first of the two sources so that it is split into two fractions that are routed respectively into at least one reference arm (38) and one measurement arm that comprises the sensing fibre (34), and, after having travelled along such arms, are recombined to produce an optical differential interference output; and
    at least one mean for injecting the light of the second source in the measurement arm of the interferometer (27) so that to locally produce perturbations of the excitation light by stimulated Brillouin scattering;
    at least one mean (73) to measure the interference signal at least at one of the differential outputs of the interferometer (27); and
    at least one control and analysis mean (53) suitable to analyse the interference signal in the frequency domain versus the sweeping of the wavelength of the sources and also at multiple different wavelength shifts between the primary and secondary sources.

2. An apparatus according to claim 1 characterized by the fact of comprising at least one mean of commutation (57) of the optical circuit and/or controllable optical attenuator suitable to enable or disable the injection of the second radiation in the measurement arm of the interferometer (27), in order to switch the working mode of the apparatus between a "Wavelength-Scanning Brillouin Optical Frequency Domain Analyser (WS-BOFDA)" mode and a (Rayleigh) "Optical frequency Domain Reflectometer (OFDR)" mode.

3. An apparatus according to claim 1 characterized by the fact that the secondary source comprises at least one Brillouin ring laser (14) that is seeded by the primary source and suitable to produce a radiation with wavelength $\Delta_P + \Delta \lambda(T_b)$ shifted with respect to that $\Delta_P$ of the primary source of a quantity $\Delta \lambda(T_b)$ that is controllable through the strain and/or temperature of the Brillouin gain medium (17) of the ring circuit (14).

4. An apparatus according to claim 3 characterized by the fact of comprising at least one modulation or suppression system for the mode-hopping of the Brillouin ring laser (14) comprising at least one mode mixer active or passive and/or a system (54, 21) suitable to vary the resonance length of the Brillouin rind laser cavity, eventually with feedback from the emission intensity (47, 52, 48, 53), so that it can be properly tuned during the wavelength-sweeping process.

5. An apparatus according to the claim 3 characterized by the fact of comprising at least one purging system (55) for the output spectrum of the Brillouin ring LASER acting on the ring-type optical circuit (14) in order to accelerate the quenching of the distortion of the spectrum of the light produced in the optical circuit consequently to the wavelength-sweeping process.

6. An apparatus according to the claim 3 characterized by the fact that the Brillouin gain medium (17) of the Brillouin ring laser (14) comprises at least one silicon photonic suspended waveguide, ad/or at least one Photonic Crystal Fibre (PCF), and/or at least one optical fibre having reduced Mode Field Diameter (MDF), and/or at least one non-linear waveguide or optical fibre with enhancement of the overlapping between longitudinal photonic and phononic modes and eventually suppression of shear modes.

7. An apparatus according to claim 1 characterized by the fact of comprising at least one system for controlling the state of polarization, such as polarizer and/or polarization controller and/or de-polarizer.

8. An apparatus according to claim 1 characterized by the fact of comprising at least one mean of optical switching suitable to switch between a working mode with the sensor connected in transmission and a working mode with the sensor connected in reflection.

9. An apparatus according to claim 1 characterized by the fact of comprising at least one reflector or absorber eventually partially reflective/absorbing even in a variable and/or controllable way, connected so that to induce a stationary propagation, or non-stationary even partially, in the measurement arm of the measurement interferometer.

10. An apparatus according to claim 1 characterized by the fact of comprising at least one system for generating optical pulses connected so that to limit in the time and/or distance the interaction between the "pump" and "stimulus" radiations within the measurement arm of the measurement interferometer.

* * * * *